US00PP32344P2

(12) United States Plant Patent
Hansen

(10) Patent No.: US PP32,344 P2
(45) Date of Patent: Oct. 13, 2020

(54) ***SEDUM* PLANT NAMED 'ANGELINA'S TEACUP'**

(50) Latin Name: *Sedum rupestre*
Varietal Denomination: Angelina's Teacup

(71) Applicant: Christopher M. Hansen, Zeeland, MI (US)

(72) Inventor: Christopher M. Hansen, Zeeland, MI (US)

( * ) Notice: Subject to any disclaimer, the term of this patent is extended or adjusted under 35 U.S.C. 154(b) by 0 days.

(21) Appl. No.: 16/602,536

(22) Filed: Oct. 24, 2019

(51) Int. Cl.
*A01H 5/02* (2018.01)
*A01H 6/32* (2018.01)

(52) U.S. Cl.
USPC ..... Plt./479
CPC ..... *A01H 6/328* (2018.05)

(58) Field of Classification Search
USPC ..... Plt./479
CPC ..... A01H 6/328; A01H 5/02
See application file for complete search history.

*Primary Examiner* — Keith O. Robinson
(74) *Attorney, Agent, or Firm* — Penny J. Aguirre

(57) ABSTRACT

A new cultivar of *Sedum* plant named 'Angelina's Teacup' that is characterized by its very tight and compact plant habit that continues to be compact into winter without the use of plant growth regulators or mechanical pinching, its non-flowering habit, its heavy lateral branching, its bright gold foliage that retains its coloration into fall, and its compact and tight plant habit.

2 Drawing Sheets

Botanical classification: *Sedum rupestre.*
Variety denomination: 'Angelina's Teacup'.

BACKGROUND OF THE INVENTION

The present invention relates to a new and distinct cultivar of *Sedum rupestre* plant, known as *Sedum* 'Angelina's Teacup' referred to hereinafter by its cultivar name, 'Angelina's Teacup'. The new cultivar of *Sedum* is a hardy herbaceous perennial grown for use as a landscape and container plant and as a groundcover.

The new Invention arose from an ongoing controlled breeding program in Hudsonville, Mich. The objective of the breeding program was to develop a new cultivar of *Sedum rupestre* that is similar to the cultivar 'Angelina' (not patented) but smaller in size and non-flowering.

The Inventor made a cross in May of 2013 between unnamed and unpatented proprietary plants in the Inventor's breeding program of *Sedum rupestre*; seedling reference no. 250-5 as the female parent and seedling reference no. 250-1 as the male parent. The Inventor selected 'Angelina's Teacup', as a single unique plant amongst the seedlings that resulted from the above cross in August of 2017.

Asexual propagation of the new cultivar was first accomplished by stem tip cuttings in June of 2015 in Hudsonville, Mich. Propagation by stem tip cuttings and division has determined the characteristics to be stable and reproduced true to type in successive generations.

SUMMARY OF THE INVENTION

The following traits have been repeatedly observed and are determined to be the characteristics of the new cultivar. These attributes in combination distinguish 'Angelina's Teacup' as a unique cultivar of *Sedum.*

1. 'Angelina's Teacup' exhibits a very tight and compact plant habit that continues to be compact into winter without the use of plant growth regulators or mechanical pinching.
2. 'Angelina's Teacup' exhibits a non-flowering habit; observed over 5 years with other plants of *Sedum rupestre* observed to bloom heavily.
3. 'Angelina's Teacup' exhibits heavy lateral branching, 7 to 9 lateral branches per 72-cell plug after only 14 weeks.
4. 'Angelina's Teacup' exhibits bright gold foliage that retains its coloration into fall.

The seed and pollen parent plant of 'Angelina's Teacup' differ from 'Angelina's Teacup' in having a less compact plant habit, foliage that is duller gold in color, some flower production and less lateral branching. 'Angelina's Teacup' can also be most closely compared to the cultivars 'Angelina' and 'Lemon Ball' (not patented). 'Angelina' and 'Lemon Ball' are both similar to 'Angelina's Teacup' in having gold color foliage and in having a ground cover type plant habit. 'Angelina' differs from 'Angelina's Teacup' in having a 55% less compact plant habit, much less lateral branching, gold foliage coloration that does not last into fall, and in flowering profusely. 'Lemon Ball' differs from 'Angelina's Teacup' in being a cultivar of *Sedum mexicanum* variety, less cold hardy (U.S.D.A. Zones 8 to 10), and 55% larger in size.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date.

BRIEF DESCRIPTION OF THE DRAWINGS

The accompanying colored photographs illustrate the overall appearance and distinct characteristics of the new *Sedum*. The photographs were taken of 2-year-old plants as grown in 2-gallon containers in full sun in Hudsonville, Mich.

The photograph in FIG. 1 provides a side view of 'Angelina's Teacup' in summer.

Figure 1:
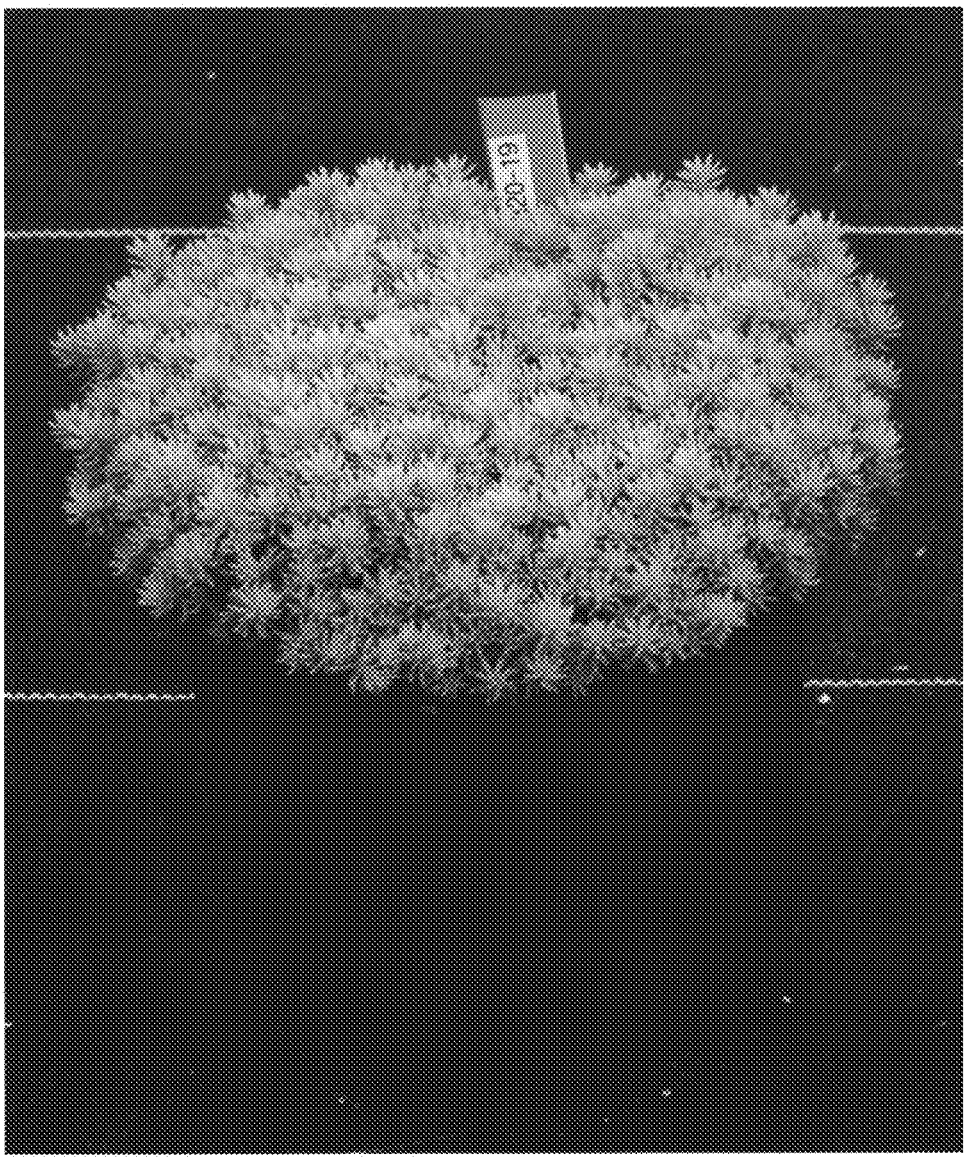
Figure 2:
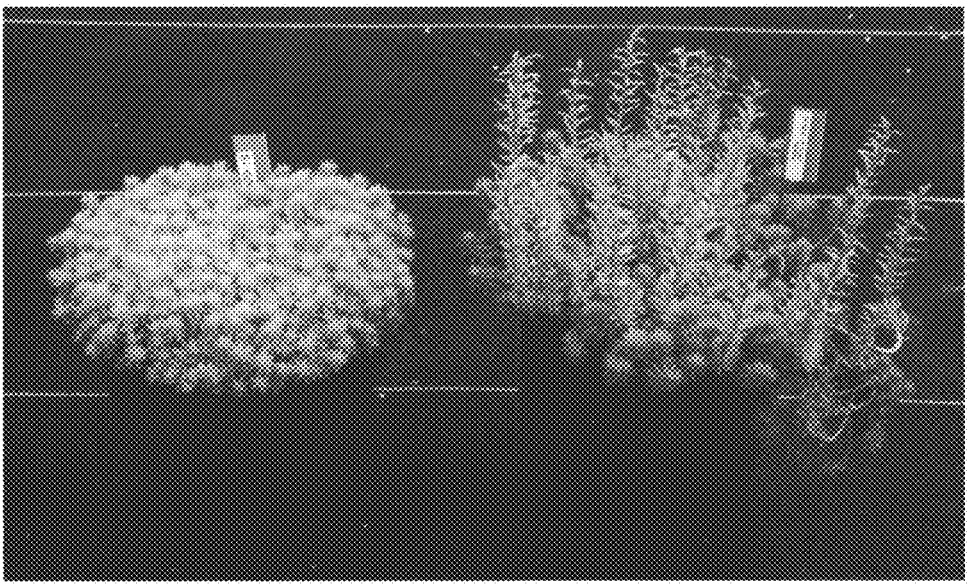

The photograph in FIG. 2 provides a comparison of 'Angelina's Teacup' (left) and 'Angelina' (right) and shows the lack of flowering stems of 'Angelina's Teacup'.

Figure 3:
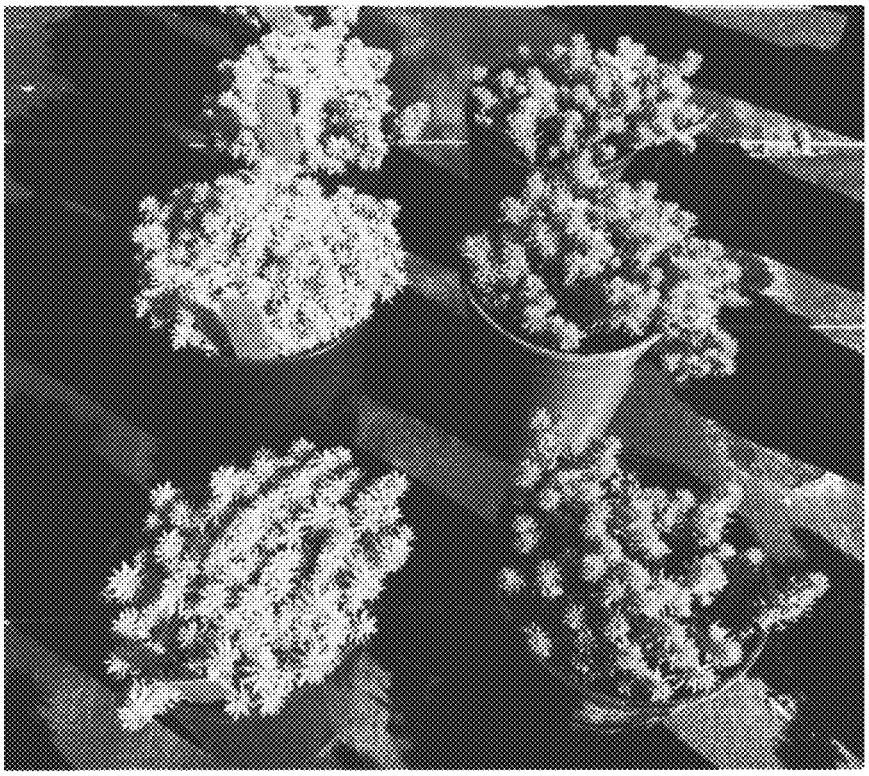

The photograph in FIG. 3 provides a comparison of 3 plants each of 'Angelina's Teacup' (left) and 'Angelina' (right) in fall and shows the difference in foliage coloration.

The colors in the photographs may differ slightly from the color values cited in the detailed botanical description, which accurately describe the colors of the new *Sedum*.

DETAILED BOTANICAL DESCRIPTION

The following is a detailed description of the new cultivar as observed on 4-month old plants as grown in 3.5-inch containers of 'Angelina's Teacup' as grown in full sun in Hudsonville, Mich. The phenotype of the new cultivar may vary with variations in environmental, climatic, and cultural conditions, as it has not been tested under all possible environmental conditions. The color determination is in accordance with The 2015 Colour chart of The Royal Horticultural Society, London, England, except where general color terms of ordinary dictionary significance are used.

General description:

*Plant type*.—Evergreen perennial.

*Plant habit*.—Dense, low growing and very compact.

*Height and spread*.—An average of 8 cm in in height and 45 cm in width as grown in the landscape.

*Hardiness*.—At least hardy in U.S.D.A. Zones 3 to 9.

*Disease and pests*.—Highly resistant to foliage blight; typically caused by the fungi *Cercospora* sp., *Collectotrichum* sp., and *Septoria* sp.

*Propagation*.—Stem tip cuttings and division.

*Root development*.—A heavily branched plant (7 to 9 lateral branches) is obtained in 14 weeks in a 72-cell plug.

*Growth rate*.—Vigorous.

Stem description:

*Stem shape*.—Round.

*Stem size*.—Average of 8 cm in length, 2 mm in width.

*Stem number*.—7 to 9 lateral branches as a young plant.

*Internode length*.—Average of 1 mm.

*Stem color*.—Mature; 145A, young; 145D.

*Stem surface*.—Glabrous, very shiny and slightly translucent, pearl-like sheen.

*Branching habit*.—Densely and very freely branched, growing in multiple angles from the base.

Foliage description:

*Leaf shape*.—Acicular.

*Leaf division*.—Simple.

*Leaf arrangement*.—Alternate.

*Leaf base*.—Truncate.

*Leaf apex*.—Acute.

*Leaf venation*.—Not conspicuous, color matched leaf color.

*Leaf margins*.—Smooth, entire.

*Leaf attachment*.—Sessile.

*Leaf aspect*.—Slightly curved downward to flexed and horizontal to stem.

*Leaf surface*.—Slightly glossy, glabrous on upper and lower surface.

*Leaf color*.—A blend of N144A and N144C with the color retained into fall with just a slight hint of 174A.

*Leaf size*.—Average of 1 cm in length, 2 mm in width.

Flower description: No flowers have been produced in 5 years of observation.

It is claimed:

1. A new and distinct variety of *Sedum* plant named 'Angelina's Teacup' as described and illustrated herein.

* * * * *